(12) United States Patent  
Satterfield et al.

(10) Patent No.: US 8,988,667 B2  
(45) Date of Patent: Mar. 24, 2015

(54) HALOGEN GAS SENSOR COMPRISING COBALT

(75) Inventors: Michael James Satterfield, Richardson, TX (US); Jeffrey R. Roubik, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 318 days.

(21) Appl. No.: 13/432,157

(22) Filed: Mar. 28, 2012

(65) Prior Publication Data

US 2013/0258347 A1 Oct. 3, 2013

(51) Int. Cl.  
*G01N 21/00* (2006.01)

(52) U.S. Cl.  
USPC ............................................. 356/72

(58) Field of Classification Search  
USPC ............................................. 356/72, 445, 213  
See application file for complete search history.

(56) References Cited

U.S. PATENT DOCUMENTS

| 7,296,458 B2 | 11/2007 | Dimeo, Jr. et al. |
| 2004/0074285 A1 | 4/2004 | Dimeo, Jr. et al. |
| 2013/0174640 A1* | 7/2013 | Oh .................................. 73/23.2 |

* cited by examiner

*Primary Examiner* — Abdullahi Nur  
(74) *Attorney, Agent, or Firm* — Jacqueline J. Garner; Frederick J. Telecky, Jr.

(57) ABSTRACT

A method of halogen gas monitoring includes contacting room air to be monitored with a halogen sensor including a cobalt or cobalt alloy layer. The halogen sensor exhibits a detectable change in at least one property upon contact with a halogen gas. A measurement from the halogen sensor is obtained after the contacting. The presence of the halogen gas is monitored based on the measurement.

18 Claims, 2 Drawing Sheets

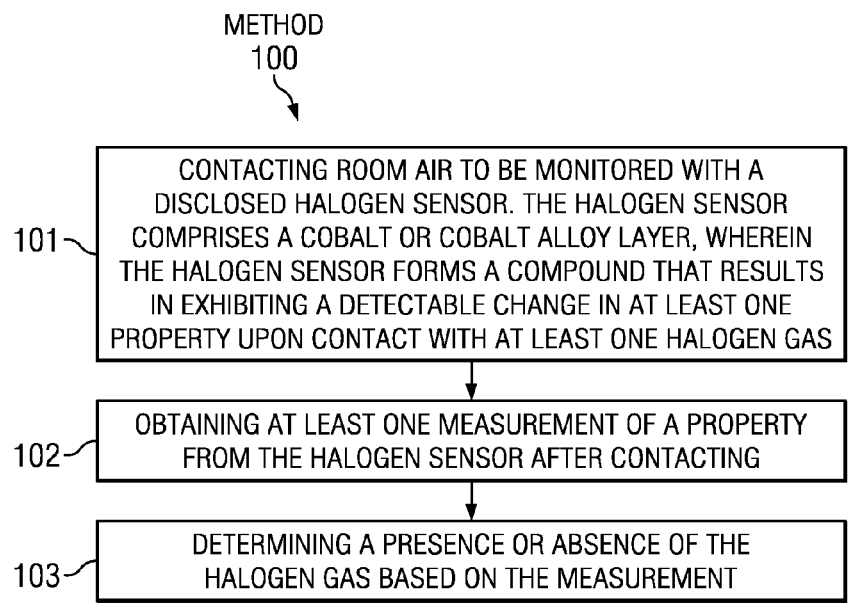
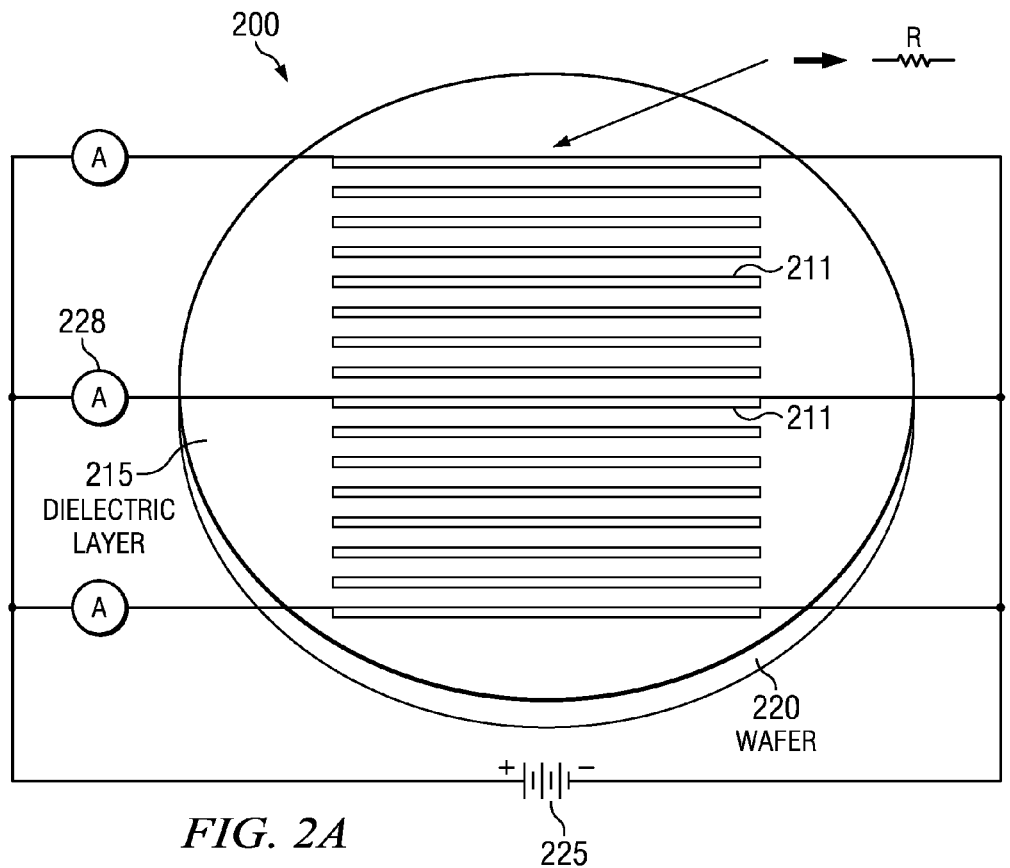

HALOGEN GAS SENSOR COMPRISING COBALT

FIELD

This disclosure relates to monitoring the halogen gas contamination in a clean room involved in fabrication of semiconductor substrates (e.g., wafers), or other high purity areas such as research laboratories.

BACKGROUND

Airborne diatomic halogen gases, such as $F_2$, $Cl_2$, $Br_2$, and $I_2$, or halogen comprising gas compounds (e.g., HCl, $NF_3$, $SiF_4$, $C_2F_6$, and HF), and activated species thereof, are known to cause corrosion on metal leads of semiconductor devices, or on certain metal layers or metal layer stacks, which can result in yield loss. In a high purity setting, halogens can contaminate a highly controlled atmosphere. What is needed is a methodology and sensing apparatus that can detect halogen comprising gases at lower levels and/or faster than known methods and apparatus/systems.

SUMMARY

Disclosed embodiments include halogen gas sensors that comprise a cobalt or cobalt alloy layer that forms a non-volatile cobalt comprising compound upon contact with a gas species comprising at least one halogen (hereafter a "halogen gas"). Formation of the cobalt comprising compound results in a detectable change in at least one property as compared to the pre-contact property of the cobalt or cobalt alloy, at lower levels and/or faster than known methods. For example, disclosed halogen gas sensors quickly form cobalt compounds in the presence of a halogen gas in as little as 2 hours or less, at estimated minimum concentrations as low as 0.002 parts per million (ppm). Disclosed properties that can be detected include electrical, optical, mass change, or other properties that provide a detectable change upon halogen gas contact.

BRIEF DESCRIPTION OF THE DRAWINGS

FIG. 1 is a flow chart showing steps for a method of sensing the presence of at least one target halogen gas in a clean room or another high purity environment, according to an example embodiment.

FIG. 2A shows a depiction of an example resistive halogen sensor system for sensing a halogen gas, according to an example embodiment.

DETAILED DESCRIPTION

Figure 2B:
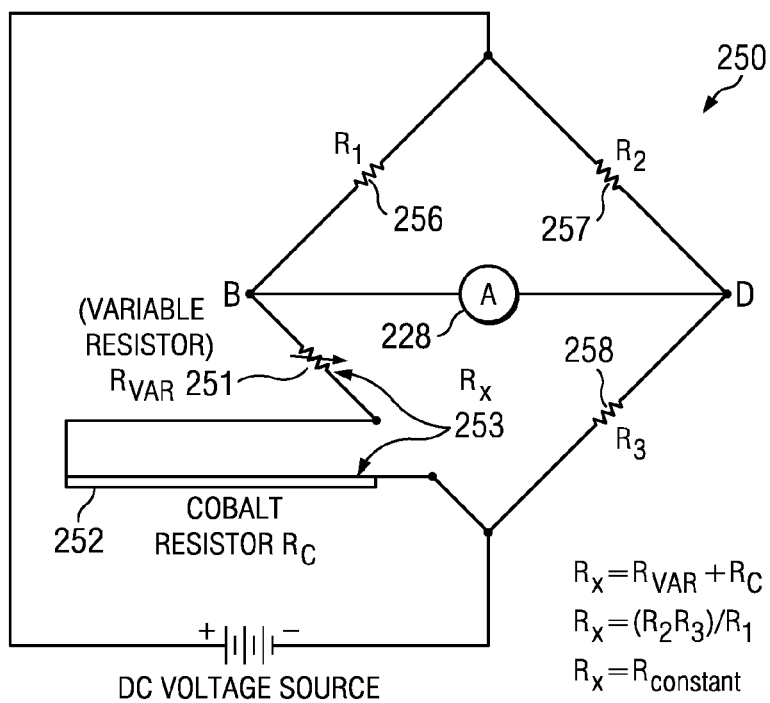
FIG. 2B shows a depiction of an example resistive halogen sensor system for sensing a halogen gas configured in a Wheatstone bridge arrangement, according to yet another embodiment.

Example embodiments are described with reference to the drawings, wherein like reference numerals are used to designate similar or equivalent elements. The drawings are not necessarily drawn to scale. Illustrated ordering of acts or events should not be considered as limiting, as some acts or events may occur in different order and/or concurrently with other acts or events. Furthermore, some illustrated acts or events may not be required to implement a methodology in accordance with this disclosure.

Disclosed embodiment include a method 100 of sensing the presence of at least one target halogen gas in a clean room or another high purity environment (e.g., laboratory for scientific research), according to an example embodiment. Method 100 may be practiced in a clean room used for semiconductor fabrication. As known in the art, clean rooms include high-efficiency particulate air (HEPA) and/or ultra-low penetration air (ULPA) filters to remove internally generated contaminants, to provide a low level of environmental pollutants such as dust, airborne microbes, aerosol particles and some chemical vapors. Such filters generally do not filter halogen gases.

Step 101 comprises contacting room air to be monitored with a disclosed halogen sensor. The halogen sensor comprises a cobalt or cobalt alloy layer, wherein the halogen sensor forms a compound that results in exhibiting a detectable change in at least one property upon contact with at least one halogen gas. When embodied as a cobalt alloy layer, cobalt generally comprises at least 50 wt. % of the alloy. The property can be an electrical property, and optical property, or a physical property (e.g., mass or density). The halogen sensor can be formed on a suitable substrate, such as a dielectric coated silicon wafer. Some polysilicon gate CMOS processes use cobalt films for siliciding the gate polysilicon, as well as on the source and drains of the MOS transistors, that facilitates obtaining a disclosed cobalt or cobalt alloy layer. Although disclosed sensor are described for sensing halogen gases, disclosed sensors may also be used to sense other gaseous species that cause cobalt to corrode. The air flow in the room or area alone can provide the driving force to flow the surrounding gases to the disclosed halogen sensor. A fan can also be used to increase the rate of gas contact with the halogen sensor.

Step 102 comprises obtaining at least one measurement of a property from the halogen sensor after the contacting. Step 103 comprises determining a presence or absence of the halogen gas based on the measurement. In one embodiment, method 100 is entirely automatic, and provides real-time monitoring. However, disclosed embodiments can include manual portions, including transportation of the halogen sensor to a measurement station, or when the measurement is based on a color change observed by an individual.

The property for which the detectable change is monitored is generally based on elemental cobalt before halogen gas exposure forming a cobalt salt with the halogen. Four dihalide salts of cobalt(II) are known to be cobalt(II) fluoride ($CoF_2$, pink), cobalt(II) chloride ($CoCl_2$, blue), cobalt(II) bromide ($CoBr_2$, green), cobalt(II) iodide ($CoI_2$, blue-black). These cobalt halides exist as anhydrous and hydrates. Whereas the anhydrous dichloride is blue, the hydrate is red. As noted above, the detectable change can be based on optical measurements, resistance measurements, or mass/density measurements. Moreover, as noted above, in one particular optical embodiment, a human observer can monitor for a color change to determine the presence of the halogen. For automatic sensing embodiments, a detectable change in the measured property can be integrated into the factory (e.g., clean room) monitoring system, and alarms and/or alerts triggered in real-time upon a detection event.

In a clean room used for semiconductor fabrication, there are a plurality of different semiconductor process tools that use chemicals comprising various halogen gases, such as plasma-based etchers. Diatomic halogen gases, such as $F_2$, $Cl_2$, $Br_2$, $I_2$, or halogen gas compounds (e.g., HCl, $NF_3$, $SiF_4$, $C_2F_6$ and HF), and activated species thereof, are generally used in semiconductor processing equipment, and if released even in trace concentrations, are known to cause corrosion on metal leads of semiconductor devices, which can cause to yield loss. Certain liquid chemicals when spilled in the clean room can cause halogen species to be introduced to the clean room atmosphere, such as hydrofluoric acid (HF), hydrochloric acid (HCl) and ammonium fluoride ($NH_3F$). Moreover, certain bases are generally also used in the clean room such as ammonia and hydroxides such as tetramethylammoniumhydroxide $(CH_3)_4NOH$ and ammonium hydroxide ($NH_4OH$), which can combine with certain halogen species to release halogens into the atmosphere, especially in the upper High-Efficiency Particulate Air (HEPA) filters where pure water is generally misted to raise humidity levels in the clean room. Such water in the upper HEPA filters can become part of a hydrolyzing reaction that releases halogens into the atmosphere.

The halogen sensor can be positioned in a variety of locations in the clean room. Typical locations are generally those separate form processing equipment, that are at or near atmospheric pressure (760 torr, with "near" atmospheric pressure being 760 torr±5%, such as a slight positive pressure), such as on the walls, ceilings, and/or aisles in the clean room.

In one particular embodiment the halogen sensor is located within a storage Pod or Front Opening Unified Pod (Foup), with optional holes added to the walls of the Pod or Foup. The halogen gas detector system that can be small enough so that the entire sensor system including its battery can be fit within the storage Pod or Foup. In the embodiment the halogen sensor comprises the cobalt or cobalt alloy layer on a semiconductor wafer, the arrangement may be referred to as a "witness" wafer. A plurality of product wafers (e.g., product wafers) can be within the storage Pod or Foup along with the witness wafer in a wafer cassette, all typically oriented horizontally within the slots of the wafer cassette.

FIG. 2A shows a depiction of an example resistive halogen sensor system 200, according to an example embodiment. Halogen sensor system 200 includes a plurality of cobalt or cobalt alloy resistor strips 211 (hereafter resistors 211) on a dielectric layer 215 that is on a substrate shown as a semiconductor wafer 220, such as a silicon or silicon/germanium wafer. There is no heating generally required for resistive halogen sensor system 200 to provide sensitivity to halogen gases to allow detection thereof.

As shown, the resistors 211 can be measured by using a DC voltage source 225 with an ammeter in series to enable measuring the DC current. When the resistors 211 are exposed to a halogen gas corrosion of the resistors 211 commences to form a cobalt halogen salt. The cobalt halogen salt has a higher bulk resistivity ($\rho$) as compared to cobalt, that will increase the resistance (R) of the resistors 211, since R is proportional to $\rho$. Changes in measured resistance thus indicate presence of a halogen gas which can be measured with either the ammeter (e.g., galvanometer) 228 in series with the DC voltage source 225, or as described below relative to FIG. 2B by using a Wheatstone bridge with a disclosed resistor positioned in one arm of the bridge.

Physical vapor deposition (PVD), such as sputtering, can be used to deposit resistors 211 of a metal such as cobalt or a cobalt alloy onto the dielectric layer 215 coated wafer 220 using a shadow mask to define strips of the cobalt or cobalt alloy during the PVD process. PVD (e.g., sputter) together with a shadow mask solves the problem of being unable to photolithographically pattern/etch cobalt resistor strips since the halogens involved in etching to form the strips due to their high reactivity to cobalt tend to completely remove the cobalt strips. In one embodiment, after formation of the resistors 211, one or more halogen sensor chips are singulated from the wafer 220, followed by packaging in non-halogen packs (ceramic) such that the lid on the package remains open. Traditional bonding methods can be used to connect the circuit to the pins of the halogen sensor chip, such as gold ball bonding, and the bond pads themselves can be formed as part of the shadow mask.

In one embodiment the resistors 211 comprises a Ti layer/ on a Co layer, having a thickness of 100 to 200 A each. For clean room applications, a thin titanium or other capping layer on the cobalt layer may be used that matches the layer stack used to form a silicide layer on the semiconductor wafers being processed in the clean room. In another embodiment, the resistors 211 consist of only a cobalt or cobalt alloy layer, such as being 100 to 200 A thick.

In another restive halogen sensor arrangement, a voltage divider circuit is configured with a fixed conventional resistor (e.g., aluminum or copper) in series with a disclosed cobalt or cobalt alloy comprising resistor. Measurement of the voltage across the disclosed cobalt or cobalt alloy comprising resistor, given the resistance of the fixed resistor, allows calculation of the resistance of the disclosed cobalt or cobalt alloy comprising resistor.

FIG. 2B shows a depiction of an example resistive halogen sensor system 250 in a Wheatstone bridge arrangement, according to yet another disclosed resistive halogen sensor embodiment. Halogen sensor system 250 may be formed analogously to halogen sensor system 200 by including at least one cobalt or cobalt alloy resistor strip on a dielectric layer on semiconductor wafer, along with some non-cobalt resistive strips. A Wheatstone bridge is known to be an electrical circuit for measuring an unknown electrical resistance by balancing two legs of a bridge circuit, one leg of which includes the unknown component.

In the Wheatstone bridge arrangement shown, $R_x$ 253 includes a variable resistor ($R_{Var}$) 251 in series with a cobalt or cobalt alloy resistor shown as a "cobalt resistor" (Rc) 252 in one of the legs. $R_1$ 256, $R_2$ 257 and $R_3$ 258 are resistors of known resistance in the other 3 legs of the Wheatstone bridge. $R_{Var}$ 251 is used to balance the Wheatstone bridge before halogen exposure so the respective resistance in all the legs are equal, resulting in the voltage between the two midpoints B and D to be zero, so that no measurable current will flow through ammeter 228. $R_{Var}$ 251 is included because the sensitivity of the Wheatstone bridge would otherwise require essentially exact values of resistance for $R_1$ 256, $R_2$ 257 and $R_3$ 258 to equal Rc 252 to null the bridge, that would be difficult. During system setup, $R_{Var}$ 251 can be varied until there is no current through the ammeter 228, which then reads zero. Detecting zero current with an ammeter 228 can be done to high accuracy.

In operation, very small changes in Rx 253 through changes in Rc 252 disrupt the balance of the Wheatstone bridge, to allow current to flow that can be detected. A small change in Rc 252 induced by halogen gas contact will force current to flow either right to left or left to right across the center points, and thus be detected by ammeter 228. Alternatively, if $R_1$ 256, $R_2$ 257 and $R_3$ 258 are known, but $R_{Var}$ 251 is not adjustable, the voltage difference across or current flow through the meter can be used to calculate the value of $R_x$, using Kirchhoffs circuit laws (also known as Kirchhoffs rules).

Figure 3:
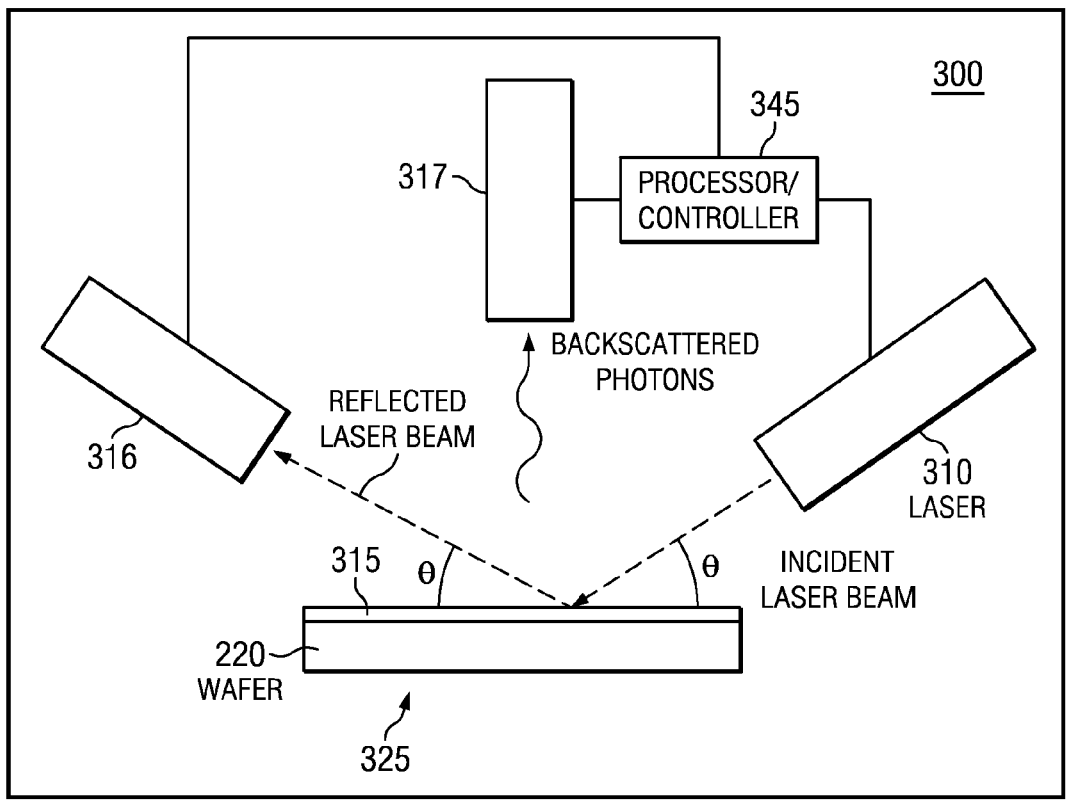
FIG. 3 shows a depiction of an example optical sensor system for sensing a halogen gas comprising a coated mirror wafer including cobalt in the coating, according an example embodiment.

FIG. 3 shows a depiction of an example optical halogen sensor-based system 300 comprising a minor wafer 325 comprising a coating 315 comprising cobalt or a cobalt alloy on a wafer 220, according an example embodiment. The coating 315 is generally unpatterned and need not be on a dielectric layer. A light source such as the laser 310 shown illuminates the coating 315 with light (e.g., ultraviolet, visible, infrared) at a given angle e in incidence. A first photodetector 316 that has photodetectors sensitive to the wavelength of light provided by the laser 310 is positioned to collect the reflected laser light and a second photodetector 317 is positioned to detect the backscattered laser light. It is also possible to use as single photodetector for optical halogen sensor-based system 300.

Two photodetectors 316, 317 to allow detection of both reflected and scattered light may be beneficial as compared to a single photodetector, however. If the surface of the coating 315 is perfectly shiny (essentially 100% reflective) the percentage of reflected light will equal the percentage transmitted. However as the surface of the coating 315 changes upon halogen gas exposure the percentage of reflected light will drop, and the percentage of scattered light will increase enabling each photodetector 316, 317 to detect changes. The reflected channel associated with photodetector 316 will drop in intensity while the scattered channel associated with photodetector 317 will increase in intensity. This arrangement is similar to the way a laser based particle counter measures haze on a wafer surface in a clean room.

Photodetectors 316 and 317 can comprise photomultipliers and/or phototransistor or photodiode arrays. System 300 is shown including a processor/controller block 345 coupled to the laser 310 and the photodetectors 316 and 317 to receive and provide electronic and digital signal processing of the measurement signals. Processor/controller block 345 enables automatic monitoring for the presence of a halogen gas based on comparing the measurement signals to stored predetermined limits. For example, processor/controller block 345 can be programmed with one or more threshold levels to allow automatic halogen gas monitoring, with the option for generating an alarm or transmitting the detection information to a central supervisory computer that controls the clean room.

The mirror wafer 325 can be replaced as needed to keep the system 300 working correctly. A cobalt minor wafer with a thin ~100 Å silicon oxide or silicon nitride film on the coating 315 comprising cobalt or a cobalt alloy can be fashioned to preserve the reflectiveness of the minor wafer by blocking gas permeation to the cobalt or a cobalt alloy, thus preventing corrosion. This special minor wafer can be used for calibration purposes. Silicon oxide generally performs better than silicon nitride for this purpose since silicon oxide has a lower index of refraction which reduces absorbance at various wavelengths as compared to higher index materials such as silicon nitride.

In another optical sensing embodiment, minor wafer 325 is used with a standard defect inspection tool (e.g., a laser based or bright field die-to-die comparison type tool) as the sensor to allow monitoring for a change in the surface of the wafer as it is exposed to the environment. At pre-read, the mirror wafer 325 has very few defects on it. After the minor wafer 325 is exposed to clean room air, such as while in a wafer cassette or face up in a wafer puck, if a halogen gas is present in the air, spots will form all over the coating 315 on the minor wafer 325. The defect inspection tool will sense these spots and a change in the post defect counts on the mirror wafer 325 can be measured. In most cases (e.g., using a red dot for each defect) the wafer map generated by the inspection tool will have a few red dots pre-read, and will nearly be solid red at the end if a halogen gas, such as $F_2$ or $Cl_2$, is present in the air.

Disclosed halogen sensors provide an unexpected result as evidenced by their comparatively high sensitivity to halogen gases (e.g., minimum detectable concentrations as low as 0.002 ppm), as compared to other metal-based halogen sensors. For example, under certain test conditions disclosed halogen gas sensors have been found to rapidly detect the presence of a halogen gas, while a wide variety of other metal coating compositions including tungsten, titanium-tungsten, titanium nitride, titanium, copper, tantalum, tantalum nitride, aluminum, nickel, alloys of nickel such as nickel platinum, and platinum were found to all fail to detect the halogen gas.

Experiments were also performed to evaluate the response of an example resistive halogen sensor comprising a rectangular resistor stripe having about 100 Å of a TiN layer on a 100 Å cobalt layer, on a silicon wafer, having a layer of silicon oxide between the wafer and the resistor. A cotton swab was used to apply chlorine bleach (a solution of approximately 3-6% sodium hypochlorite (NaClO)) to the surface of the resistors. A hand held ohmmeter was used for the resistance measurements. The resistance of the resistor was 886Ω before applying the bleach. After 3 hours and 11 minutes the resistance of the resistor increased to 25.4 kΩ. After 7 hours and 11 minutes the resistance of the resistor increased to 5.01 MΩ, which is almost a 4 order of magnitude increase as compared to the resistance before halogen exposure.

Those skilled in the art to which this disclosure relates will appreciate that many other embodiments and variations of embodiments are possible within the scope of the claimed invention, and further additions, deletions, substitutions and modifications may be made to the described embodiments without departing from the scope of this disclosure.

We claim:

1. A method of halogen gas monitoring, comprising:
   contacting room air to be monitored with a halogen sensor comprising a cobalt or cobalt alloy layer, wherein said halogen sensor exhibits a detectable change in at least one property upon contact with at least one halogen gas;
   obtaining a measurement from said halogen sensor after said contacting, and
   monitoring for a presence of said halogen comprising species based on said measurement.

2. The method of claim 1, wherein said halogen sensor is positioned in a location that is at or near atmospheric pressure.

3. The method of claim 1, wherein said halogen sensor is located in a clean room where a plurality of semiconductor process tools that use chemicals comprising said halogen gas are located.

4. The method of claim 1, wherein said property is an optical property, said halogen sensor comprises an optical halogen sensor, and said measurement comprises an optical measurement.

5. The method of claim 4, wherein a semiconductor defect inspection tool is used for said obtaining said measurement.

6. The method of claim 4, wherein a laser illuminates said halogen sensor and a first photodetector is positioned to collect reflected laser light and a second photodetector is positioned to detect backscattered laser light.

7. The method of claim 1, wherein said property is an electrical property, said halogen sensor comprises a resistive halogen sensor system, and said measurement comprises an electrical measurement.

8. The method of claim 7, wherein said resistive halogen sensor is arranged within a Wheatstone bridge circuit.

9. The method of claim 1, wherein said halogen sensor comprises a layer comprising titanium on said cobalt or said cobalt alloy layer on a wafer.

10. A system for halogen gas monitoring, comprising:
    a halogen sensor comprising a cobalt or cobalt alloy layer on a substrate, wherein said halogen sensor exhibits a detectable change in at least one property upon contact with at least one halogen gas, and a measurement system, comprising:
  a source for applying an energetic stimulus to said halogen sensor, and
  a detector for obtaining a measurement responsive to said energetic stimulus.

11. The system of claim 10, wherein said substrate has a dielectric layer thereon and said cobalt or cobalt alloy layer is on said dielectric layer.

12. The system of claim 10, wherein said property is an optical property, said halogen sensor comprises an optical halogen sensor, and said measurement system comprises an optical measurement system.

13. The system of claim 12, wherein said optical measurement system comprises a semiconductor defect inspection tool.

14. The system of claim 12, wherein said source of said optical measurement system comprises a laser for illuminating said optical halogen sensor and said detector comprises a first photodetector positioned to collect reflected laser light and a second photodetector positioned to detect backscattered laser light.

15. The system of claim 10, wherein said property is an electrical property, said halogen sensor comprises a resistive halogen sensor, said source comprises a voltage source, and said measurement system comprises an electrical measurement system.

16. The system of claim 15, wherein said electrical measurement system includes a Wheatstone bridge circuit, and wherein said resistive halogen sensor is in one leg of said Wheatstone bridge circuit.

17. The system of claim 10, wherein said halogen sensor comprises a layer comprising titanium on said cobalt or said cobalt alloy layer on said substrate.

18. The system of claim 10, further comprising a processor/controller block coupled to said source and to said detector for processing said measurement and for automatic monitoring for a presence of said halogen gas based comparing said measurement to stored predetermined limits.

\* \* \* \* \*